(12) United States Patent
Steiner et al.

(10) Patent No.: US 6,508,818 B2
(45) Date of Patent: Jan. 21, 2003

(54) BONE ANCHORING ASSEMBLY WITH A SNAP-IN BALLHEAD

(75) Inventors: Beatrice Steiner, Cham (CH); Max Aebi, Québec (CA)

(73) Assignee: Synthes (U.S.A.), Paoli, PA (US)

( * ) Notice: Subject to any disclaimer, the term of this patent is extended or adjusted under 35 U.S.C. 154(b) by 31 days.

(21) Appl. No.: 09/788,483

(22) Filed: Feb. 21, 2001

(65) Prior Publication Data

US 2001/0007941 A1 Jul. 12, 2001

Related U.S. Application Data

(63) Continuation of application No. PCT/CH98/00360, filed on Aug. 21, 1998.

(51) Int. Cl.[7] .............................................. A61B 17/56
(52) U.S. Cl. ........................................................ 606/69
(58) Field of Search ............................... 60/61, 69, 70, 60/71, 72, 73

(56) References Cited

U.S. PATENT DOCUMENTS 4,484,570 A * 11/1984 Sutter et al. ............. 128/92 D
4,537,185 A    8/1985  Stednitz
5,015,247 A    5/1991  Michelson
5,129,901 A    7/1992  Decoste
5,860,973 A    1/1999  Michelson
6,156,037 A   12/2000  LeHuec et al.

FOREIGN PATENT DOCUMENTS

| DE | 867 422 | 1/1953 |
|----|---------|--------|
| DE | 297 10 979 | 8/1997 |
| EP | 0 809 975 | 12/1997 |
| GB | 231 155 | 7/1925 |
| GB | 2 294 399 | 5/1996 |
| WO | WO 96/08206 | 3/1996 |
| WO | WO 88/03781 | 6/1998 |

* cited by examiner

Primary Examiner—Eduardo C. Robert
(74) Attorney, Agent, or Firm—Pennie & Edmonds LLP

(57) ABSTRACT

A bone anchoring assembly includes at least one fixation plate and at least one bone anchoring element. Each bone anchoring element includes a circular-cylindrical hollow body with upper and lower ends, a hemi-spherical connector that is pivotably mounted to and supported by fixation elements, an external thread that extends partially along the outer surface of the body for anchoring the bone anchoring element into the cortical portion of the bone, and a series of teeth located on the lower end of the body for cutting into the bone.

48 Claims, 3 Drawing Sheets

BONE ANCHORING ASSEMBLY WITH A SNAP-IN BALLHEAD

CROSS REFERENCE TO RELATED APPLICATIONS

This application is a continuation of the U.S. National Stage designation of co-pending International Patent Application PCT/CH98/00360, filed Aug. 21, 1998, the entire content of which is expressly incorporated by reference.

FIELD OF THE INVENTION

The invention relates to a bone-anchoring assembly. More particularly, the invention relates to bone anchoring elements that are capable of being pivotably attached to osteosynthesis fixation plates or longitudinal support bars for the fixation of bone segments such as vertebrae.

BACKGROUND OF THE INVENTION

Implants for fixation of bones such as bone plates, longitudinal support bars, pedicle screws, and bone anchoring assemblies increasingly are used in osteosynthesis applications. Such devices are useful for treating fractures of bones, for anchoring bone segments, or for providing support to bones weakened from disease or defect.

One such implant is disclosed in the German utility model DE 297 10 979 to Aesculap. The implant comprises a bone anchoring element that is insertable into a bone segment. The bone anchoring element can then be mounted using a detachable ball clamp to a connection element. The connection element, in turn, can be clamped to a longitudinal support or to another bone anchoring element. By connecting several bone anchoring elements together, bone segments or vertebra can be rigidly connected together. As disclosed in the German utility model, the anchoring elements are in the form of hollow, cylindrical bone screws that have an external threaded and are fitted with radial boreholes located between the threads. A ball joint pivotably supports the bone screw in the connection element until the ball joint is locked by the ball clamp. However, the drawback to the disclosed implant is the dish-shaped seat of the ballhead of the bone screw only allows inserting the bone screw unilaterally from above into the connection element and, as a result, the bone screw and connection element must be screwed jointly into the bone.

PCT publication no. WO 96/08206 to Foley discloses an osteosynthesis device with an elongated bone fixation plate and several bone anchoring elements. The disclosed bone anchoring elements consist of bone screws with spherical and radially elastic screw heads. The bone screws are inserted into the fixation plate at the desired angle and conical fixation screws are inserted into the spherical screw head of the bone fixation screw, thereby radially expanding the screw head and fixing the screw at the desired angle in the bone plate. The drawback to the disclosed osteosynthesis device is that the bone screws must be actively supported at the desired angle of insertion until they can be fixed with the conical fixation screws. As a result, the disclosed device is difficult to implant.

A similar drawback is present in the osteosynthesis device disclosed in PCT publication no. WO 88/03781 to Raveh. The disclosed osteosynthesis device comprises a bone fixation plate and several bone screws used to fix the plate to the desired bone area. The bone screws disclosed in this application are inserted into the bone fixation plate at the desired angle and conical fixation screws are then inserted into the bone screw heads to expand and lock the bone screw heads into the bone fixation plate. Again, the drawback to the disclosed osteosynthesis device is that the bone screws must be actively supported at the desired angle of insertion until they can be fixed with the conical fixation screws.

Another osteosynthesis device comprising a bone fixation plate and bone fixation means is disclosed in published EPO application no. EP 0 809 075 to Benzel. The bone fixation means disclosed comprises a bone screw with a spherical head and a hollow shaft that is configured and dimensioned to threadably receive a bone expansion screw. The bone screw is inserted through the bone fixation plate at the desired angle into the bone and the bone expansion screw is then inserted into the bone screw to expand and lock the bone screw in at the desired angle in the bone plate and the bone. However, the drawback to this device is the same as the above devices in that the bone screws must be actively supported at the desired angle of insertion until they can be fixed with the bone expansion screws.

In light of the foregoing, it is clear that there exists a need for an improved bone anchoring element.

SUMMARY OF THE INVENTION

The present invention relates to a bone anchoring assembly having at least one bone anchoring element capable of being attached to at least one osteosynthesis plate or bar for the fixation of bone segments. The at least one bone anchoring element preferably includes a circular-cylindrical body with a hemi-spherical connecting element at the posterior or upper end of the body for coupling to another fixation element, a flange located at the upper end of the body for limiting the insertion depth of the bone anchoring element, a plurality of radial borehole passages located on the body of the bone anchoring element, an external, self-tapping thread that extends over a portion of the bone anchoring element, and teeth at the anterior or lower end of the body for cutting into bone.

In one preferred embodiment, the bone anchoring element consists of a circular-cylindrical hollow body fitted at one end with a hemi-spherical connector that is mounted concentrically with the bone anchoring element's central axis. The hemi-spherical connector is configured and dimensioned to be pivotably coupled to another fixation element such as a bone fixation plate or longitudinal support bars. Specifically, the hemi-spherical connector comprises a number of resilient blades, arranged in a circular pattern, that are radially displaceable either toward or away from the central axis of the bone anchoring element which allows the connector to be compressed or expanded thereby allowing it to snap into or out of a receiving cavity of the fixation element. Preferably, the connector blades are formed by slits running parallel to the central axis of the bone anchoring element along the periphery of the spherical connector. In addition, since the connector is shaped as a hemi-sphere and is radially deformable, the bone anchoring element can be pivotably coupled and supported in the receiving cavity of the fixation element.

The hemi-spherical connector, preferably, has a diameter D, a height of U, and a ratio of U/D that is between 0.4 and 0.7. Furthermore, the radially displaceable blades are elastically variable in a range between 0.95 to 1.05 of the diameter D. The connector can also be fixed at a particular position or angle through the use of conical fixation screws. The connector has a conically tapering bore located concentrically to the central axis of the bone anchoring element in which a conical fixation screw can be threadably received.

Typically, the bone anchoring element is snapped into a receiving cavity of another implantable element and is positioned at the desired angle. A conical fixation screw is then inserted through the implantable element into the threaded bore located in the connector. As the conical fixation screw is tightened, the blades of the spherical connector are displaced outwardly locking the bone anchoring element at the desired angle to the implantable element.

In another preferred embodiment, the outside surface of the anterior or lower portion of the anchoring element does not contain an external thread allowing for a smooth surface with radial borehole passages. The radial borehole passages allow the osteoinductive material located within the hollow anchoring body to fuse with the bone located outside the anchoring body. In addition, the radial borehole passages reduce the amount of material needed to create the implant, thereby substantially lowering the total weight of the bone anchoring element.

In a further preferred embodiment, the bone anchoring apparatus comprises bone anchoring elements and plates fitted with receiving means the spherical connectors of the bone anchoring elements. The receiving means essentially consist of spherical cavities appropriately sized to allow the hemi-spherical connectors to snap into the cavity and be pivotably supported in the plate. Also, the bone anchoring element is detachably affixed to the plate by bone anchoring fasteners such as screws or nuts. Typically, the connector allows a 15° to 35° angular range of pivotal motion for the bone anchoring element with respect to the axis orthogonal to the plate surface. Each plate also has an elongated central channel that extends along a central axis, across most of the length of the plate, capable of receiving a fastener that will affix the plates together at any distance along the central axis within the central channel. Typically, the distance the two plates are displaceable from each other ranges between 20 mm to 60 mm. The fastener is preferably a screw or a bolt and the plates preferably have textured surfaces at their respective points of contact to prevent slippage of the plates with respect to each other and to increase the stability of the affixed plates. In addition, the plates preferably have lateral lugs to further prevent slippage and to prevent rotation of the plates with respect to each other.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENT

Figure 1:
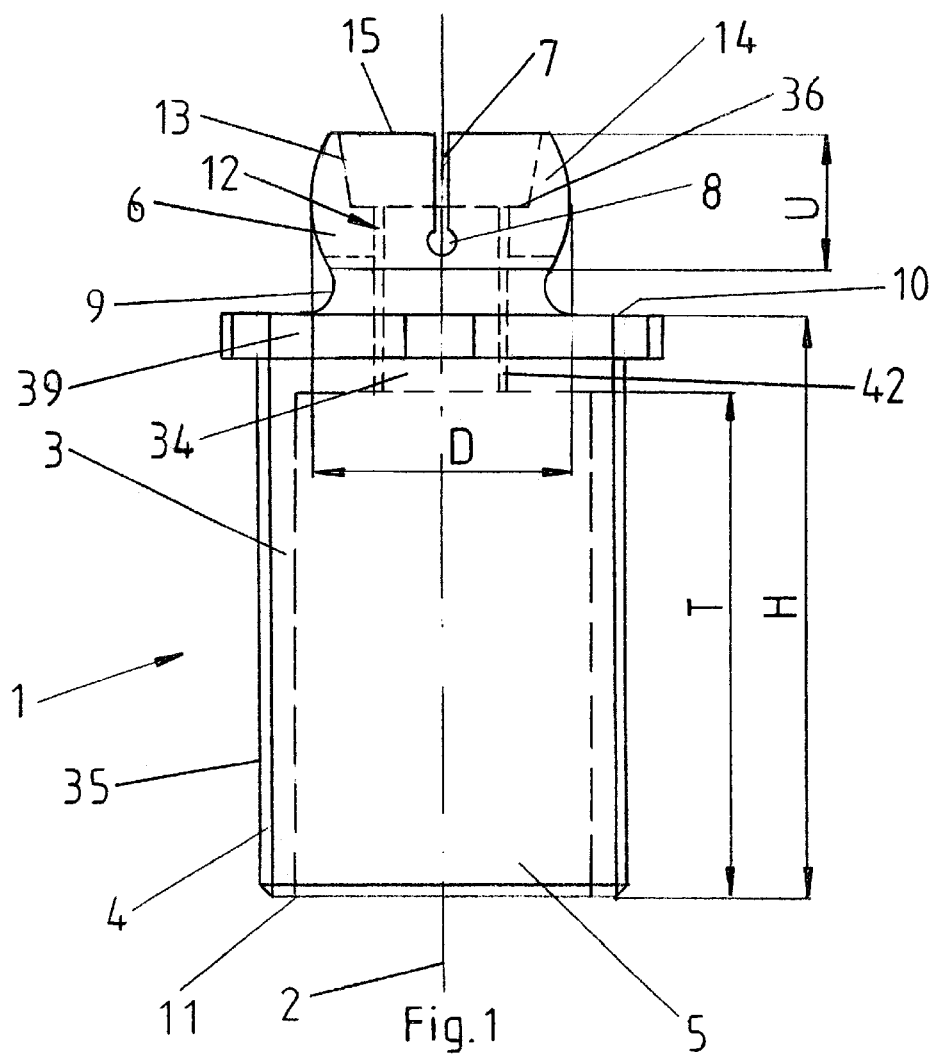
FIG. 1 shows a schematic view of a bone anchoring element of the present invention.
Figure 2:
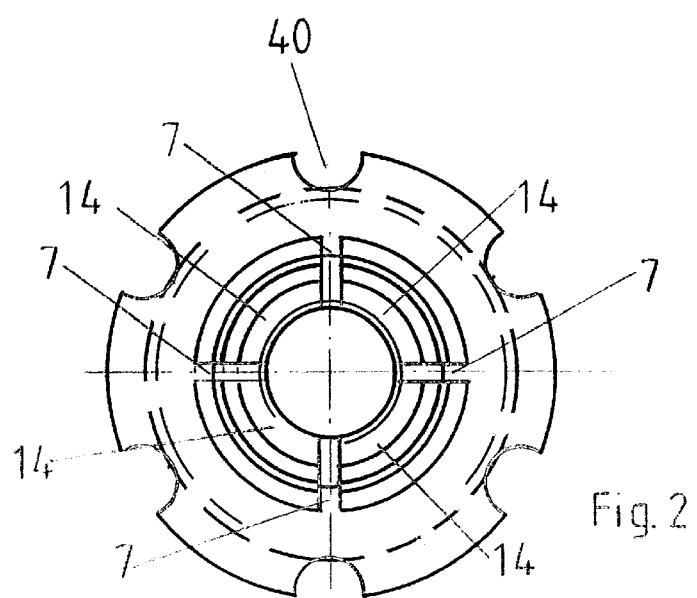
FIG. 2 shows a top view of the bone anchoring element of FIG. 1.

Referring to FIGS. 1 and 2, bone anchoring element 35 of bone anchoring assembly 1 is shown schematically. In a preferred embodiment, bone anchoring element 35 comprises circular-cylindrical body 3, hemi-spherical connector 6, and flange 39. Circular-cylindrical body 3 defines a central axis 2 and upper end 10 and lower end 11.

Connector 6 is attached directly to circular-cylindrical body 3 via semi-circular lathed surface 9 at upper end 10 and is located coaxially to central axis 2 of circular-cylindrical body 3. Connector 6 has resilient blades 14 which are formed by slits 7 running parallel to axis 2 and terminating in borehole 8. In addition, connector 6 includes connection and expansion mechanisms comprising conically lathed surface 13 and borehole 34 with threads 12. Conically lathed surface 13 tapers inward starting from end face 15 and terminating at shoulder 36. Thread 12 begins near shoulder 36 and terminates near end 42 and allows for a conical fixation screw to be screwed into borehole 34.

Circular-cylindrical body 3 has a certain height, designated as H. Circular-cylindrical body 3 also has concentric borehole 5 which, measured from lower surface 11, has a depth of T. Thus, circular-cylindrical body 3 is hollow over a length corresponding to the depth of T. The outer surface of circular-cylindrical body 3 is smooth over the anterior or lower portion of circular-cylindrical body 3 while the remaining portion of the outer surface contains an external thread and, accordingly, is not smooth. At upper end 10, circular-cylindrical body 3 is fitted with flange 39 which has a diameter larger than the diameter of circular-cylindrical body 3. Flange 39 is fitted with six equidistant semicircular notches 40 located on the periphery of flange 39. Using notches 40 on flange 39 with a matching tool, bone anchoring element 35 can be rotated into the bone. Alternatively, in place of notches 40, flange 39 can be shaped hexagonally and with a matching hexagonal tool, bone anchoring element 35 can be rotated into the bone. In addition, flange 39 ensures that bone anchoring element 35 is not rotated unduly deeply into the bone by providing a stop that prevents bone anchoring element 35 from rotating further into the bone.

Figure 3:
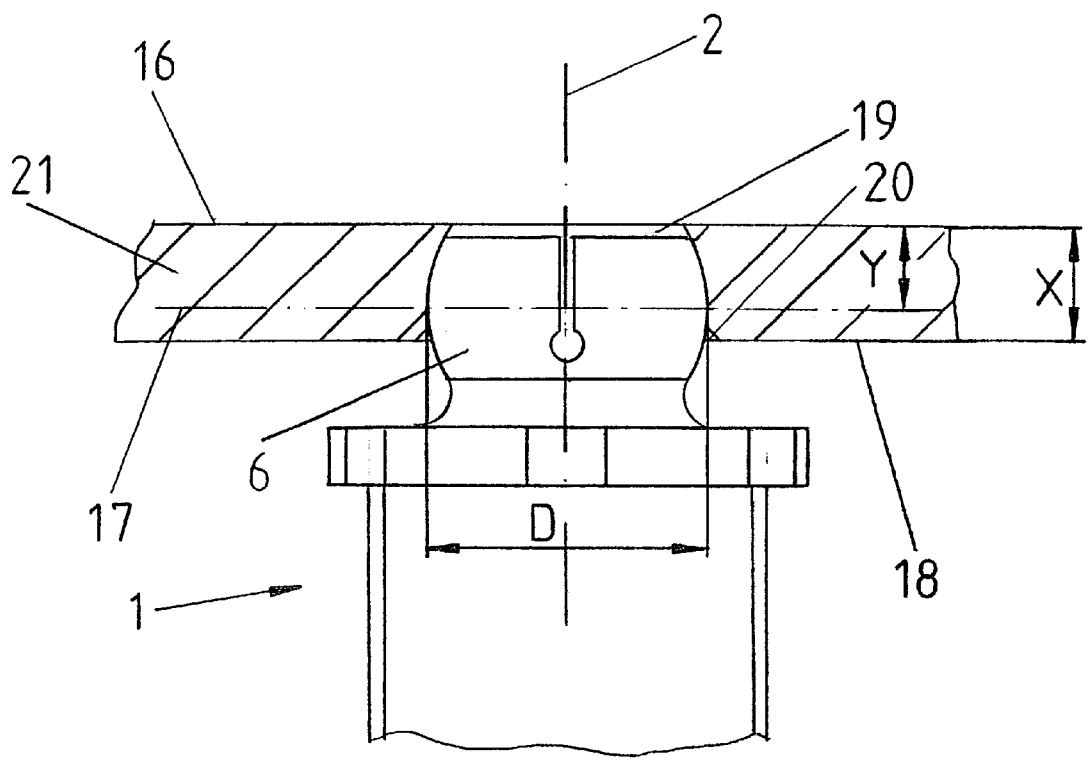
FIG. 3 shows a detailed view of the bone anchoring element of FIGS. 1 and 2 coupled to a fixation plate.

FIG. 3 shows a detailed view of connector 6 of bone anchoring element 35 coupled to a fixation plate 21. Receiving cavity 19 is spherical in shape and connector 6 can be snapped into receiving cavity 19 as a result of the elastic deformability of resilient tabs 14. Receiving cavity 19 is designed in such a manner that plane 17, which is orthogonal to central axis 2 is a distance Y<X from top surface 16 of fixation plate 21. These dimensions allow connector 6 to be pivotably coupled and supported in receiving cavity 19.

Figure 4:
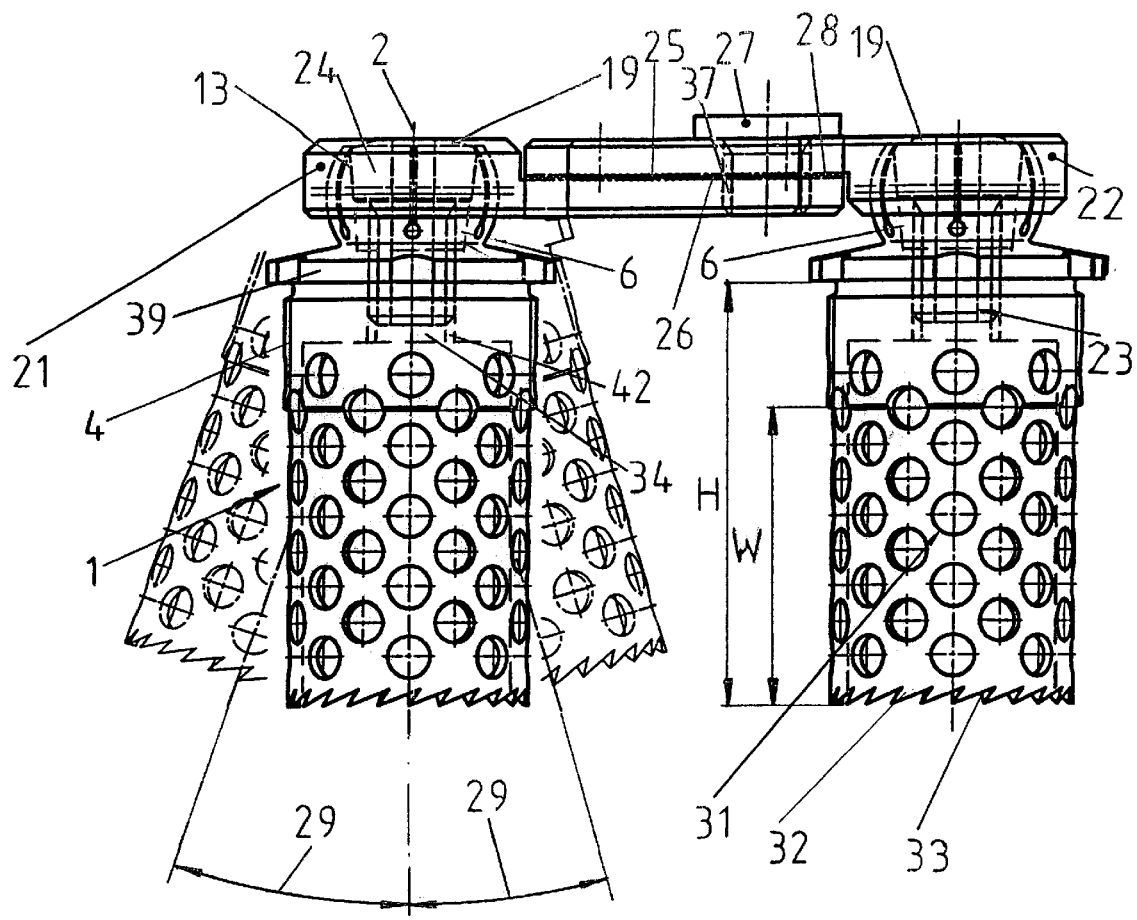
FIG. 4 shows a perspective view of a bone anchoring assembly of the present invention.
Figure 5:
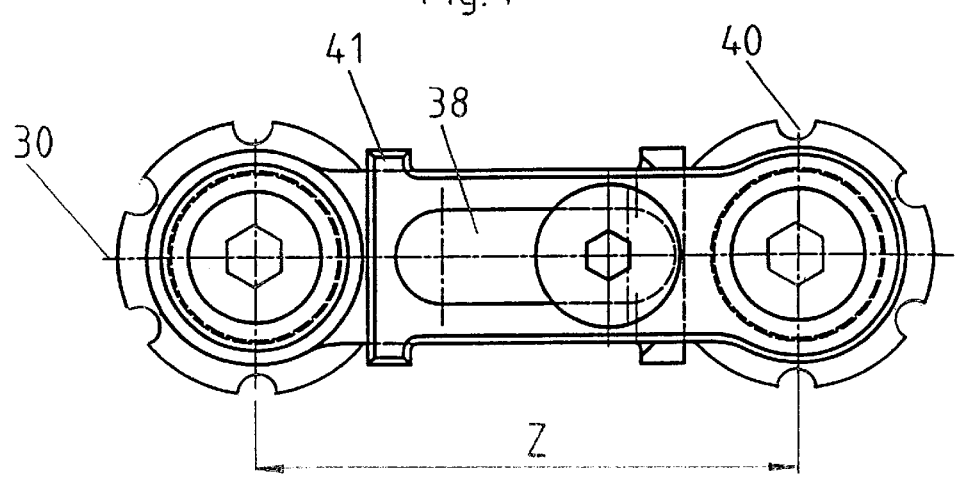
FIG. 5 shows a top view of the bone anchoring assembly of FIG. 4.

Turning now to FIGS. 4 and 5, another preferred embodiment of bone anchoring assembly 1 is shown. In this embodiment, bone anchoring assembly 1 comprises two bone anchoring elements 35 and two fixation plates 21, 22. Defined centrally along the length of fixation plates 21, 22 is central axis 30. Fixation plate 21 has contacting surface 25 that is placed in contact with contacting surface 26 of fixation plate 22 when the two fixation plates are coupled together via elongated slots 38 and fastener 27. The contacting surfaces 25, 26 are textured, typically in the form of serrations 28, to help prevent fixation plates 21, 22 from slipping when a load is placed on fixation plates 21, 22. In addition, fixation plates 21, 22 both have lateral lugs 41 which are located at the ends of contacting surfaces 25, 26. Lateral lugs 41 prevent fixation plates 21, 22 from rotating relative to each other thereby becoming skewed with respect to central axis 30.

Circular-cylindrical bodies 3 have a plurality of radial borehole passages 31 located along the outside surface of circular-cylindrical bodies 3, have external threads 4 located at the posterior or upper ends of circular-cylindrical bodies 3, and have cutting teeth 32 with radial cutting edges 33 located at the anterior or lower end of the bodies. Radial borehole passages 31 provide a passageway to allow the osteoinductive material located within the borehole of circular-cylindrical bodies 3 to communicate with the bony tissue located outside of circular-cylindrical bodies 3. External threads 4 anchor circular-cylindrical bodies 3 to the bony tissue. Circular-cylindrical bodies 3 also have flange 39 located at the posterior or upper end of the bodies. Flange 39, preferably, has six semicircular notches 40 located equidistantly along the periphery of the flange. Through the use of notches 40 and a matching tool, circular-cylindrical body 3 can be rotated into bone. Alternatively, flange 39 can be in the shape of a hexagon and a hexagonal tool can be used to rotate circular-cylindrical body 3 into bone. Further, flange 39 also acts as a stop to prevent circular-cylindrical bodies 3 from being rotated excessively deep into the bone. Circular-cylindrical bodies 3 also have connectors 6 which are used to couple circular-cylindrical bodies 3 to fixation plates 21, 22. Connectors 6 are spherical in shape with diameters that correspond to the size of the receiving boreholes 19 located in fixation plates 21, 22. Also, both connectors 6 are fitted with boreholes 34 that have internal threads 12, a conically lathed geometry 13, and a series of slits located along the periphery of connectors 6. Screws 23 are inserted into boreholes 34 through receiving boreholes 19 wherein screw heads 24 fit within the conically lathed geometry 12 to fix circular-cylindrical bodies 3 to fixation plates 21,22. More specifically, when screws 23 are tightened, resilient blades 14 of connectors 6 are clamped against the walls of receiving boreholes 19 thereby affixing circular-cylindrical bodies 3 to fixation plates 21, 22.

The structure and means for affixing the circular-cylindrical bodies 3 to fixation plates 21, 22 and for coupling fixation plates 21, 22 together allow circular-cylindrical bodies 3 to be attached at various angles and distances from each other. For example, the spherical structure of connectors 6 allow circular-cylindrical bodies 3 to be pivotably supported and attached to fixation plates 21, 22 at angle 29 which ranges from 16° inwardly from perpendicular axis 2 to 19° outwardly from perpendicular axis 2. In addition, fastener 27, which typically is in the form of a screw, is threadably received in borehole 37 which can be located any where within elongated slot 38. By using elongated slot 38 with borehole 37, fixation plates 21, 22 can be coupled together at various displacement distances Z, thereby varying the distance between circular-cylindrical bodies 3.

The insertion of the above described bone anchoring assembly does not require a previously drilled borehole or duct. The procedure for inserting and locking the bone anchoring assembly into a bone is very quick and quite simple. The first step in inserting the assembly into bone is to introduce a Kirschner wire into the bone. The Kirschner wire is used to guide circular-cylindrical bodies 3 as they are inserted into the bone. A first circular cylindrical body 3 is rotated into the bone using flange 39 and a matching tool. As circular-cylindrical body 1 is rotated into the bone, cutting teeth 32 with radial cutting edges 33 cut the bone creating bone chips which are guided into borehole 5 located within circular-cylindrical body 3. External thread 4 anchors circular-cylindrical body 3 in the bone. Since external thread 4 is present only on the upper portion of circular-cylindrical body 3, circular-cylindrical body 3 is anchored only to the cortical portion of the bone and not to the spongy portion of the bone. Furthermore, since external thread 4 does not enter into the spongy portion of the bone, external thread 4 will not harm the spongy portion of the bone through micromotion shears and notch effects. After first circular-cylindrical body 3 has been screwed into the bone, the Kirschner wire may then be removed. A second circular-cylindrical body 3 is then inserted into the bone in the same manner as first circular-cylindrical body 3. After circular-cylindrical bodies 3 have been inserted into the bone, fixation plates 21, 22 are attached to circular-cylindrical bodies 3 by snapping connectors 6 into receiving boreholes 19 and inserting screws 23 through boreholes 34 located in connectors 6 and receiving boreholes 19 located in fixation plates 21, 22. Fastener 27 is then threadably received through borehole 37 thereby coupling fixation plates 21, 22 together. Finally, the bone anchoring assembly, as a whole, can then be locked in the desired position by tightening screws 23 and fastener 27.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A bone anchoring element comprising:
    a hollow cylindrical body comprising an upper end, a lower end, and an exterior surface, the exterior surface having a threaded portion and an unthreaded portion, the unthreaded portion located substantially adjacent to the lower end of the body;
    a hemi-spherical connector with a diameter and a height mounted at the upper end of the body for coupling to a fixation device,
    wherein the connector comprises a number of resilient blades formed by a number of slits on the connector thereby allowing the connector to be elastically compressible or expandable.
2. The bone anchoring element of claim 1, wherein the threading is located substantially adjacent to the upper end of the body for anchoring the body into surrounding bony tissue.
3. The bone anchoring element of claim 2, wherein threading is self-tapping.
4. The bone anchoring element of claim 2, further comprising a plurality of radial boreholes on the external surface of the body.
5. The bone anchoring element of claim 1, further comprising at least one tooth extending from the lower end of the body for cutting bone.
6. The bone anchoring element of claim 1, further comprising a flange located at the upper end of the body for limiting insertion depth of the bone anchoring element.
7. The bone anchoring element of claim 6, wherein the flange has a plurality of notches for receiving an insertion tool.
8. The bone anchoring element of claim 6, wherein the flange is hexagonal.
9. The bone anchoring element of claim 1, wherein the connector has a borehole for receiving a fastener.
10. The bone anchoring element of claim 9, wherein an inner surface of the borehole is threaded.
11. The bone anchoring element of claim 9, wherein the borehole conically tapers from an upper end to a lower end over a portion of its length.
12. The bone anchoring element of claim 1, wherein the ratio of the height to the diameter of the connector is between 0.4 and 0.7.
13. The bone anchoring element of claim 1, wherein the blades are elastically compressible or expandable from a range of 0.95 to 1.05 times the diameter of the connector.

14. A bone anchoring assembly comprising:
the bone anchoring element of claim 1; and
a first fixation plate having a first end, a second end, and a central axis,
wherein, an elongated slot is located along the central axis at the first end of the first fixation plate and a borehole configured and dimensioned to pivotably receive and support the connector of the bone anchoring element is located at the second end of the first fixation plate.

15. The bone anchoring assembly of claim 14, wherein the bone anchoring element can pivot between 0° and 35° from a plane perpendicular to the first fixation plate.

16. The bone anchoring assembly of claim 14, further comprising:
a second bone anchoring element; and
a second fixation plate having a first end, a second end, and a central axis,
wherein an elongated slot is located along the central axis at the first end of the second fixation plate and a borehole configured and dimensioned to pivotably receive and support the second bone anchoring element is located at the second end of the plate, and
wherein the elongated slots of the first and second fixation plates are configured and dimensioned to receive a fastener thereby allowing the first and second fixation plates to be coupled together at varying separation distances along the central axis and wherein the connectors of the first and second bone anchoring elements have boreholes configured and dimensioned to receive fasteners allowing the bone anchoring elements to be detachably affixed to the first and second fixation plates.

17. The bone anchoring assembly of claim 16, wherein the separation distance between the bone anchoring elements can be varied between 20 mm and 60 mm.

18. The bone anchoring assembly of claim 16, wherein the fixation plate have lateral extension at the first end of each fixation plate for limiting the rotation of the fixation plates with respect to the central axis.

19. The bone anchoring assembly of claim 16, wherein the first end of each fixation plate is textured.

20. A bone anchoring element comprising:
a hollow cylindrical body with upper end and lower ends;
a flange located at the upper end of the body for limiting insertion depth of the bone anchoring element;
a hemi-spherical connector with a diameter and a height mounted at the upper end of the body for coupling to a fixation device,
wherein the connector comprises a number of resilient blades formed by a number of slits on the connector thereby allowing the connector to be elastically compressible or expandable.

21. The bone anchoring element of claim 20, wherein the flange is hexagonal.

22. The bone anchoring element of claim 21, wherein the flange has a plurality of notches for receiving an insertion tool.

23. The bone anchoring element of claim 20, wherein the connector has a borehole for receiving a fastener and wherein an inner surface of the borehole is threaded.

24. The bone anchoring element of claim 20, wherein the ratio of the height to the diameter of the connector is between 0.4 and 0.7.

25. The bone anchoring element of claim 20, wherein the blades are elastically compressible or expandable from a range of 0.95 to 1.05 times the diameter of the connector.

26. A bone anchoring element comprising:
a hollow cylindrical body with upper and lower ends; and
a hemi-spherical connector with a diameter and a height mounted at the upper end of the body for coupling to a fixation device,
wherein the connector comprises a number of resilient blades formed by a number of slits on the connector thereby allowing the connector to be elastically compressible or expandable and wherein the ratio of the height to the diameter of the connector is between 0.4 and 0.7.

27. The bone anchoring element of claim 26, wherein the blades are elastically compressible or expandable from a range of 0.95 to 1.05 times the diameter of the connector.

28. The bone anchoring element of claim 26, further comprising at least one tooth extending from the lower end of the body for cutting bone.

29. The bone anchoring element of claim 26, further comprising a flange located at the upper end of the body for limiting insertion depth of the bone anchoring element.

30. The bone anchoring element of claim 26, wherein the flange has a plurality of notches for receiving an insertion tool.

31. The bone anchoring element of claim 26, wherein an inner surface of the borehole is threaded.

32. A bone anchoring element comprising:
a hollow cylindrical body with upper and lower ends;
at least one tooth extending from the lower end of the body for cutting bone; and
a hemi-spherical connector with a diameter and a height mounted at the upper end of the body for coupling to a fixation device,
wherein the connector comprises a number of resilient blades formed by a number of slits on the connector thereby allowing the connector to be elastically compressible or expandable.

33. The bone anchoring element of claim 32, further comprising a plurality of radial boreholes on the external surface of the body.

34. A bone anchoring element comprising:
a hollow cylindrical body with upper and lower ends;
a hemi-spherical connector with a diameter and a height mounted at the upper end of the body for coupling to a fixation device; and
a flange located at the upper end of the body for limiting the insertion depth of the bone anchoring element,
wherein the connector comprises a number of resilient blades formed by a number of slits on the connector thereby allowing the connector to be elastically compressible or expandable and wherein the flange has a plurality of notches for receiving an insertion tool.

35. The bone anchoring element of claim 34, wherein the flange is hexagonal.

36. The bone anchoring element of claim 34, wherein an inner surface of the borehole is threaded.

37. The bone anchoring element of claim 36, wherein the body has an exterior surface, the exterior surface having a threaded portion and an unthreaded portion, the unthreaded portion located substantially adjacent to the lower end of the body.

38. The bone anchoring element of claim 34, wherein the ratio of the height to the diameter of the connector is between 0.4 and 0.7.

39. The bone anchoring element of claim 38, wherein the blades are elastically compressible or expandable from a range of 0.95 to 1.05 times the diameter of the connector.

40. The bone anchoring element of claim 34, further comprising a plurality of radial boreholes on the external surface of the body.

41. A bone anchoring assembly comprising:

a hollow cylindrical body with upper and lower ends;

a hemi-spherical connector with a diameter and a height mounted at the upper end of the body for coupling to a fixation device; and a first fixation plate having a first end, a second end, and a central axis, wherein the connector comprises a number of resilient blades formed by a number of slits on the connector thereby allowing the connector to be elastically compressible or expandable and wherein an elongated slot extending along substantially the length of the plate is located along the central axis beginning at the first end of the first fixation plate and a borehole configured and dimensioned to pivotably receive and support the connector of the bone anchoring element is located at the second end of the first fixation plate.

42. The bone anchoring assembly of claim 41, further comprising:

a second bone anchoring element; and a second fixation plate having a first end, a second end, and a central axis, wherein an elongated slot is located along the central axis at the first end of the second fixation plate and a borehole configured and dimensioned to pivotably receive and support the second bone anchoring element is located at the second end of the plate, and wherein the elongated slots of the first and second fixation plates are configured and dimensioned to receive a fastener thereby allowing the first and second fixation plates to be coupled together at varying separation distances along the central axis and wherein the connectors of the first and second bone anchoring elements have boreholes configured and dimensioned to receive fasteners allowing the bone anchoring elements to be detachably affixed to the first and second fixation plates.

43. The bone anchoring assembly of claim 41, wherein the separation distance between the bone anchoring elements can be varied between 20 mm and 60 mm.

44. The bone anchoring assembly of claim 41, wherein the first end of each fixation plate is textured.

45. The bone anchoring assembly of claim 41, wherein the fixation plates have lateral extensions at the first end of each fixation plate for limiting the rotation of the fixation plates with respect to the central axis.

46. The bone anchoring assembly of claim 41, wherein the bone anchoring element can pivot between 0° and 35° from a plane perpendicular to the first fixation plate.

47. A bone anchoring assembly comprising:

a hollow cylindrical body with upper and lower ends;

a hemi-spherical connector with a diameter and a height mounted at the upper end of the body for coupling to a fixation device; and a first fixation plate having a first end, a second end, and a central axis, wherein the connector comprises a number of resilient blades formed by a number of slits on the connector thereby allowing the connector to be elastically compressible or expandable and wherein an elongated slot is located along the central axis at the first end of the first fixation plate and a borehole configured and dimensioned to pivotably receive and support the connector of the bone anchoring element is located at the second end of the first fixation plate and wherein the width of the fixation plate near the elongated bore is approximately one half the width of the plate near the borehole.

48. A bone anchoring assembly comprising:

a hollow cylindrical body with upper and lower ends;

a hemi-spherical connector with a diameter and a height mounted at the upper end of the body for coupling to a fixation device; and a first fixation plate having a first end, a second end, and a central axis, wherein the connector comprises a number of resilient blades formed by a number of slits on the connector thereby allowing the connector to be elastically compressible or expandable and wherein an elongated slot approximately twice as long as it is wide is located along the central axis at the first end of the first fixation plate and a borehole configured and dimensioned to pivotably receive and support the connector of the bone anchoring element is located at the second end of the first fixation plate.

* * * * *